(12) United States Patent
Mark et al.

(10) Patent No.: US 8,986,334 B2
(45) Date of Patent: Mar. 24, 2015

(54) TISSUE REMOVAL DEVICE WITH TISSUE GRIP

(75) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 0 days.

(21) Appl. No.: 12/966,327

(22) Filed: Dec. 13, 2010

(65) Prior Publication Data

US 2011/0190802 A1 Aug. 4, 2011

Related U.S. Application Data

(63) Continuation-in-part of application No. 12/700,456, filed on Feb. 4, 2010, now Pat. No. 8,486,097.

(51) Int. Cl.
*A61B 17/32* (2006.01)
*A61B 17/16* (2006.01)
*A61B 10/02* (2006.01)

(52) U.S. Cl.
CPC .......... *A61B 17/1611* (2013.01); *A61B 10/0275* (2013.01); *A61B 10/0283* (2013.01)
USPC ............................. 606/171; 606/180; 606/184

(58) Field of Classification Search
USPC .......... 606/79, 80, 83, 169, 170–180
See application file for complete search history.

(56) References Cited

U.S. PATENT DOCUMENTS

| 3,990,453 | A | | 11/1976 | Douvas et al. |
| 4,258,716 | A | * | 3/1981 | Sutherland .................... 606/170 |
| 4,440,170 | A | * | 4/1984 | Golden et al. ................. 606/142 |
| 4,848,338 | A | * | 7/1989 | De Satnick et al. ............... 606/1 |
| RE33,258 | E | * | 7/1990 | Onik et al. ...................... 604/22 |
| 5,269,797 | A | | 12/1993 | Bonati et al. |
| 5,273,519 | A | | 12/1993 | Koros et al. |
| 5,304,203 | A | * | 4/1994 | El-Mallawany et al. ...... 606/207 |
| 5,385,570 | A | * | 1/1995 | Chin et al. ..................... 606/170 |
| 5,505,210 | A | * | 4/1996 | Clement ....................... 600/566 |
| 5,526,822 | A | | 6/1996 | Burbank et al. |
| 5,603,724 | A | | 2/1997 | O'Connor |
| 5,653,713 | A | | 8/1997 | Michelson |

(Continued)

FOREIGN PATENT DOCUMENTS

| DE | 935625 C | 11/1955 |
| DE | 4424659 A1 | 1/1996 |

(Continued)

OTHER PUBLICATIONS

Non-Final Office Action dated Nov. 14, 2011 for U.S. Appl. No. 12/700,378.

(Continued)

*Primary Examiner* — Tuan V Nguyen

(74) *Attorney, Agent, or Firm* — Kristin L. Murphy; Brooks Kushman P.C.

(57) ABSTRACT

A tissue removal device is disclosed. In one arrangement, the tissue removal device includes a cutting member operatively connected to an actuator assembly and a fixed member. The cutting member is configured to slide with respect to the fixed member in a reciprocating manner. The fixed member includes an upwardly extending foot plate that defines a contact surface that is configured with an uneven texture that serves as a grip to operatively retain material to be cut when the cutting member is moved toward the foot plate.

29 Claims, 11 Drawing Sheets

(56) References Cited

U.S. PATENT DOCUMENTS

| | | | |
|---|---|---|---|
| 5,702,420 A | 12/1997 | Sterling et al. | |
| 5,797,958 A * | 8/1998 | Yoon | 606/207 |
| 6,132,448 A | 10/2000 | Perez et al. | |
| 6,875,173 B2 | 4/2005 | Suddaby | |
| 6,887,240 B1 * | 5/2005 | Lands et al. | 606/51 |
| 2004/0102783 A1 | 5/2004 | Sutterlin et al. | |
| 2007/0208271 A1 | 9/2007 | Voegele | |
| 2007/0233133 A1 | 10/2007 | Cohen et al. | |
| 2009/0048622 A1 | 2/2009 | Wilson | |
| 2011/0190801 A1 | 8/2011 | Mark et al. | |

FOREIGN PATENT DOCUMENTS

| | | |
|---|---|---|
| WO | WO-03037194 A1 | 5/2003 |
| WO | WO-2005011505 A1 | 2/2005 |
| WO | WO-2005063126 A2 | 7/2005 |
| WO | WO-2008024684 A2 | 2/2008 |

OTHER PUBLICATIONS

PCT International Search Report dated Jan. 9, 2012 for PCT/US2011/023766.

Response to Non-Final Office Action dated Nov. 14, 2011 for U.S. Appl. No. 12/700,456.

Response to Non-Final Office Aciton dated Nov. 14, 2011 for U.S. Appl. No. 12/700,378.

Non-Final Office Action dated Nov. 14, 2011 for U.S. Appl. No. 12/700,456.

Final Office Action dated May 25, 2012 for U.S. Appl. No. 12/700,456.

Response to Non-Final Office Action dated May 25, 2012 for U.S. Appl. No. 12/700,456.

Non-Final Office Action dated Aug. 7, 2012 for U.S. Appl. No. 12/700,456.

Response to Non-Final Office Action dated Aug. 7, 2012 for U.S. Appl. No. 12/700,456.

Notice of Allowance dated Mar. 13, 2013 for U.S. Appl. No. 12/700,456.

LinkBio—Spine Instruments for SimpleCleanTM; at http://linkbio.com/LinkSpinalInstruments/simpleclean.htm dated Feb. 9, 2010.

Catalog for ClearFlushTM entitled Flushable Kerrison Rongeur; by Boss Instruments Ltd. Jan. 2007.

Webpage for Collagen Matric, Inc. entitled Science, Technology, Innovation dated Feb. 9, 2010 at www.collagematrix.com.

Wecome to Spinus, LLC—Inovators of Devices for Neurological and Orthopedic Surgery product ANDRE™; dated Feb. 9, 2010 at http://www.psinus.us/Product-Information/andre2.htm.

Pictures of Surgical Instruments—Kerrison Punch from www.surgical-instrument-pictures.com dated Feb. 9, 2010.

Publication for Aesculap Neurosurgery Pneumatic Kerrison, by Caroli et al.; publisher: Braun Sharing Expertise (2008).

Webpage from ComMed Linvatec—Manual Instruments at http://www.conmed.com/products_maninst_shutt.php dated Feb. 9, 2010.

Catalog for Fehling Surgical Instruments, Inc..for Ejector Punches and Accessories.

* cited by examiner

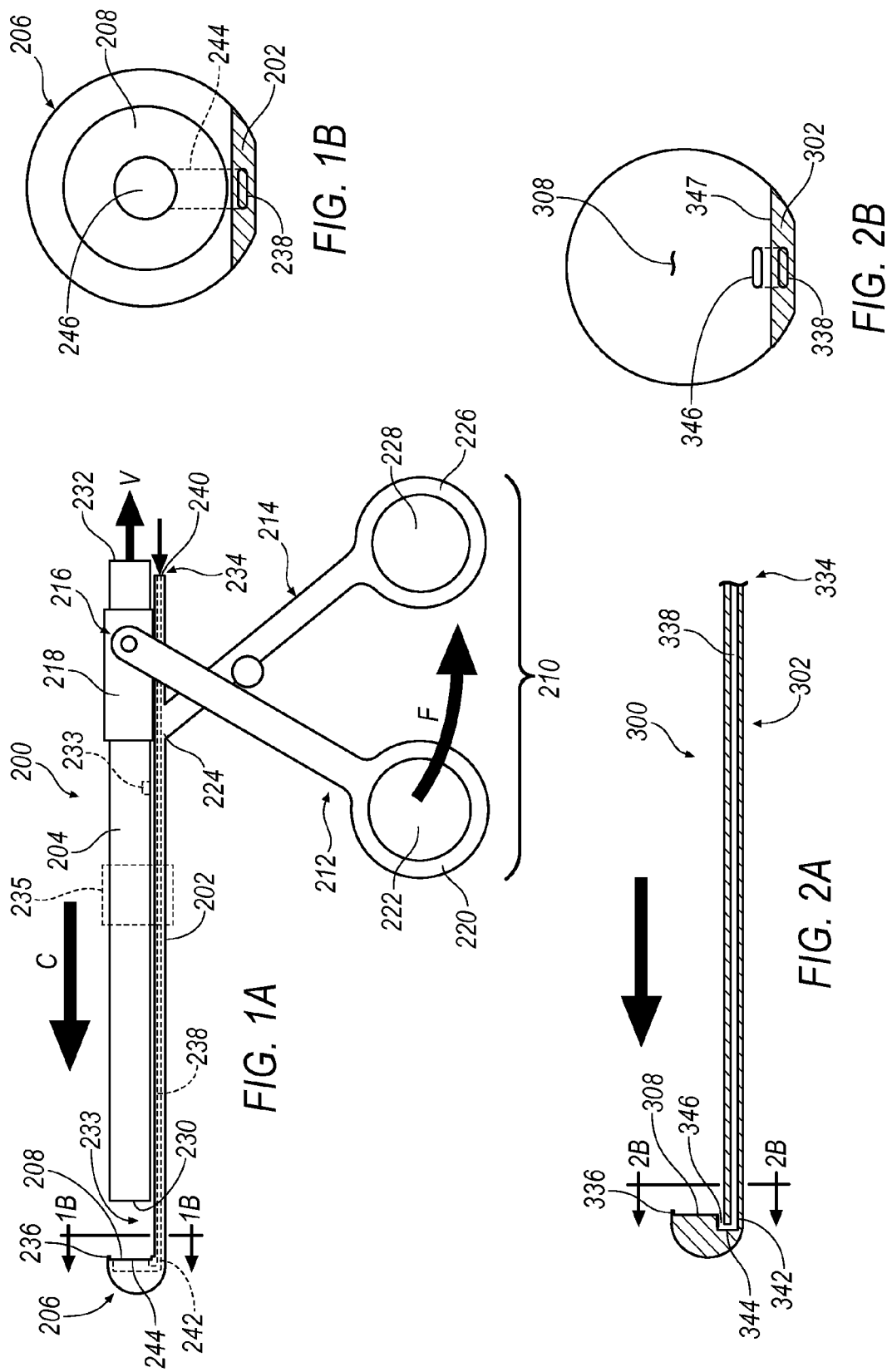

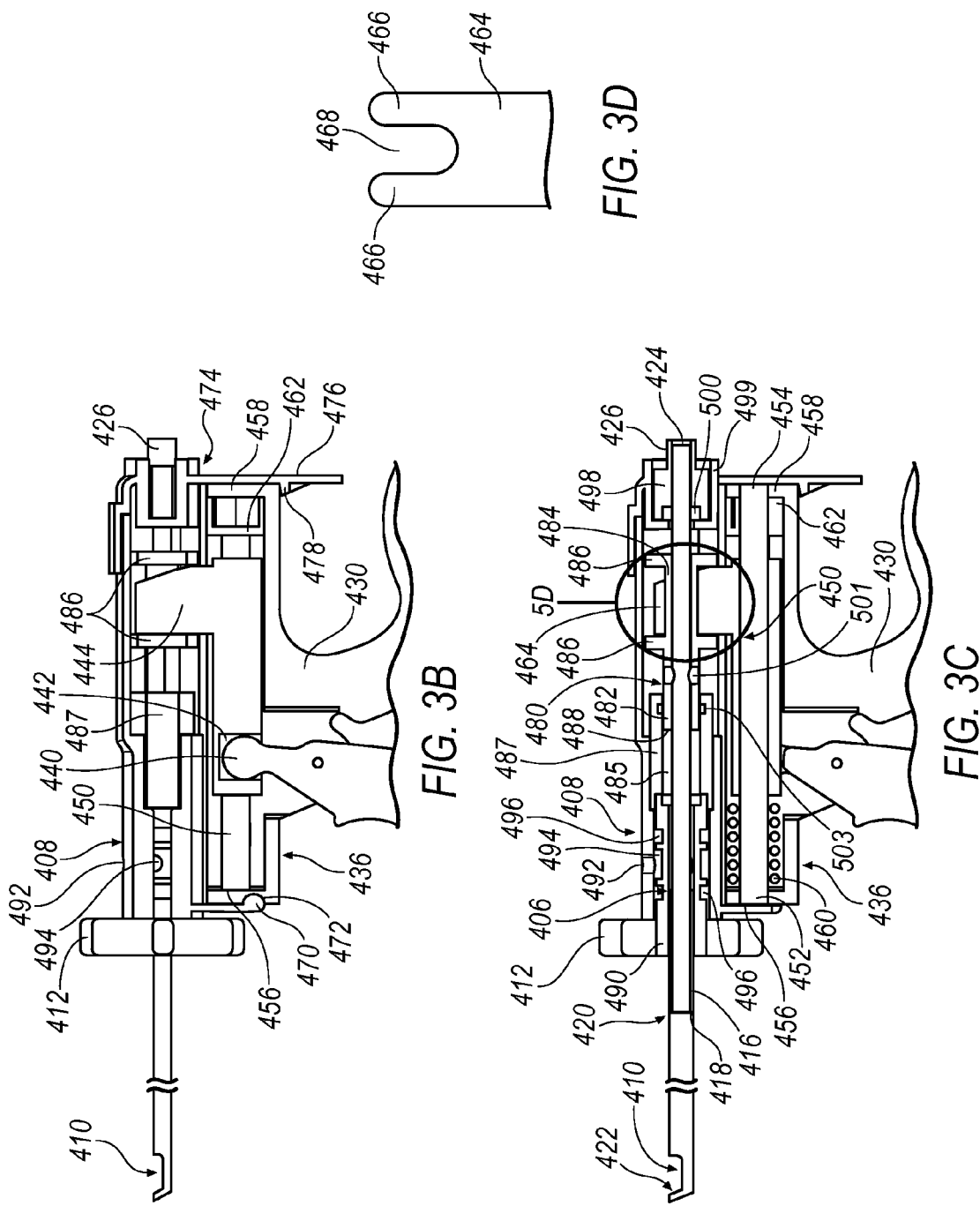

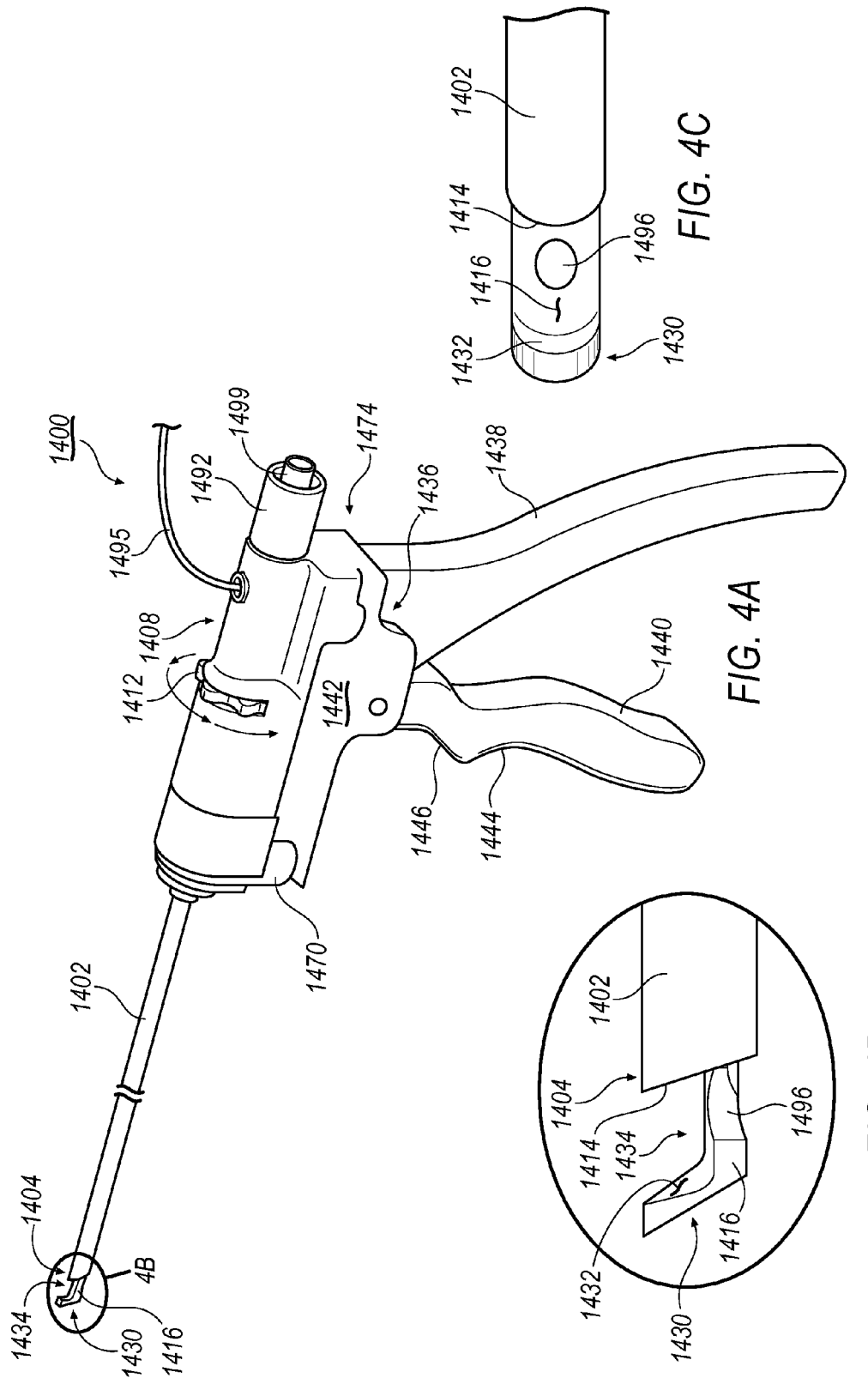

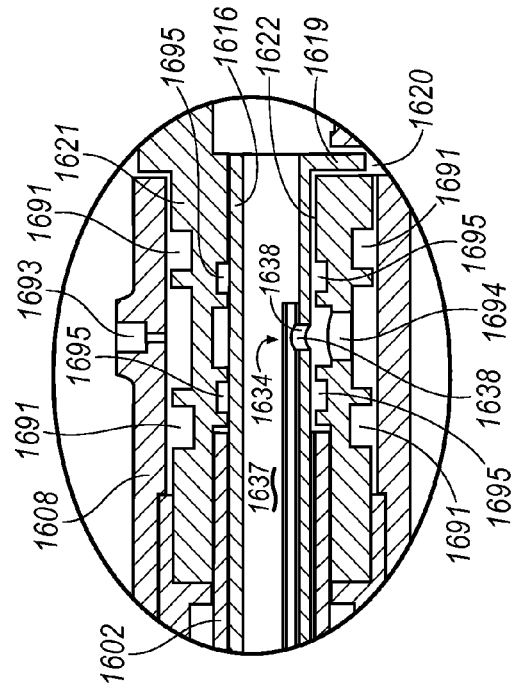
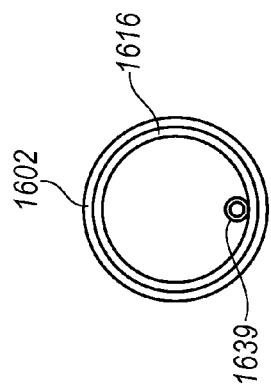
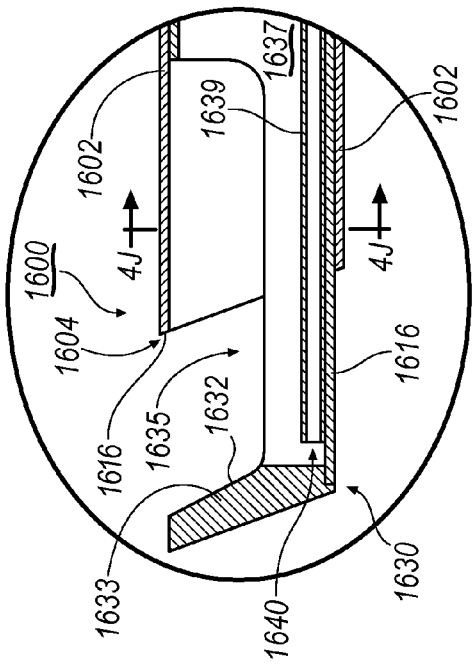

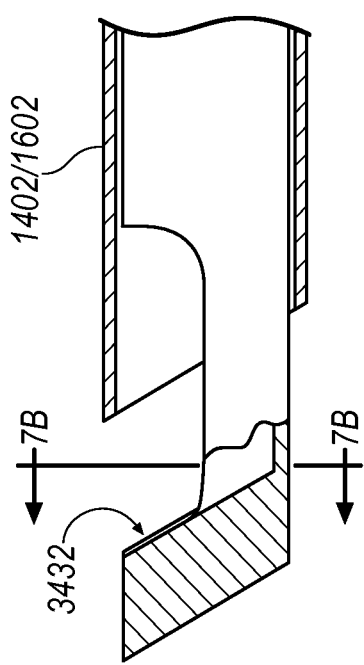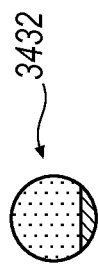

TISSUE REMOVAL DEVICE WITH TISSUE GRIP

CROSS-REFERENCE TO RELATED APPLICATIONS

This application is a Continuation-in-part of U.S. patent application Ser. No. 12/700,456 filed on Feb. 4, 2010, which is now U.S. Pat. No. 8,486,097, the contents of which are incorporated by reference in its entirety.

TECHNICAL FIELD

The present disclosure relates to a tissue removal device.

BACKGROUND

Punch type forceps, referred to as rongeurs or kerrison type cutters, have been employed in a variety of medical procedures that call for excising tissue and even bony material. Such medical procedures include, for example, endoscopic procedures. Typical known forceps include a sharp cutter, or punch, that is positioned at a distal end of a hollow tube. The proximal end of the hollow tube is connected to hand grips that are squeezed together to move the punch against a footplate. In operation, when the hand grip is not actuated, a gap is formed between the footplate and the cutter. Tissue and/or bony material enters the gap and the hand grips are actuated to move the cutter against the footplate, thereby severing tissue and/or bone material that is positioned in the gap.

The foot plate in most prior art designs are configured such that the foot plate includes either a 40° angle or a 90° angle. These designs were created to address a variety of clinical needs and challenges associated with accessing tissue to enable effective cutting of tissue. For example, the 40° angle foot plate is most prominently used because it affords the ability to get under a tissue surface. More specifically, the foot plate is used as a shovel. However, gristle tissue, harder bone, and even softer tissue may slip out of the gap between the foot plate and the cutter, and off the foot plate, as the cutter is advanced towards the foot plate.

BRIEF DESCRIPTION OF THE DRAWINGS

Exemplary embodiments of the present disclosure will now be described in greater detail with reference to the attached figures, in which:

FIG. 1A is a side elevational view of an irrigating suction device.

FIG. 1B is a cross-sectional view of the irrigating suction device of FIG. 1A taken along lines 3B-3B.

FIG. 2A is a cross-sectional view of an alternative embodiment of an irrigating suction device.

FIG. 2B is a cross-sectional view of the irrigating suction device of FIG. 2A taken along lines 2B-2B.

FIG. 3B is a partial cross-sectional view of an actuating portion of the irrigating suction device of 3A.

FIG. 3C is another partial cross-sectional view of the actuating portion of the irrigating suction device of FIG. 3A.

FIG. 3D is an end view of area 3D from FIG. 3C.

FIG. 4A is a perspective view of an alternative embodiment of an irrigating suction device.

FIG. 4B is an enlarged side view of area 4B from FIG. 4A.

FIG. 4C is top view of a distal end of the irrigating suction device of FIG. 4A.

FIG. 4I is a partial cross-sectional view of a distal end of an alternative arrangement of an irrigation suction punch.

FIG. 4J is a cross-sectional view of the distal end taken along lines 4J-4J of FIG. 4I.

FIG. 4K is a partial cross-sectional view of an alternative arrangement of a saline hub.

FIG. 7A is a partial cross sectional view of an alternative configuration for a distal end of the irrigation suction punch such as that illustrated in either FIGS. 4A-4H or FIGS. 4I-4K.

FIG. 7B is an end view of the foot plate taken along lines 7B-7B in FIG. 7A.

DETAILED DESCRIPTION

Figure 3A:
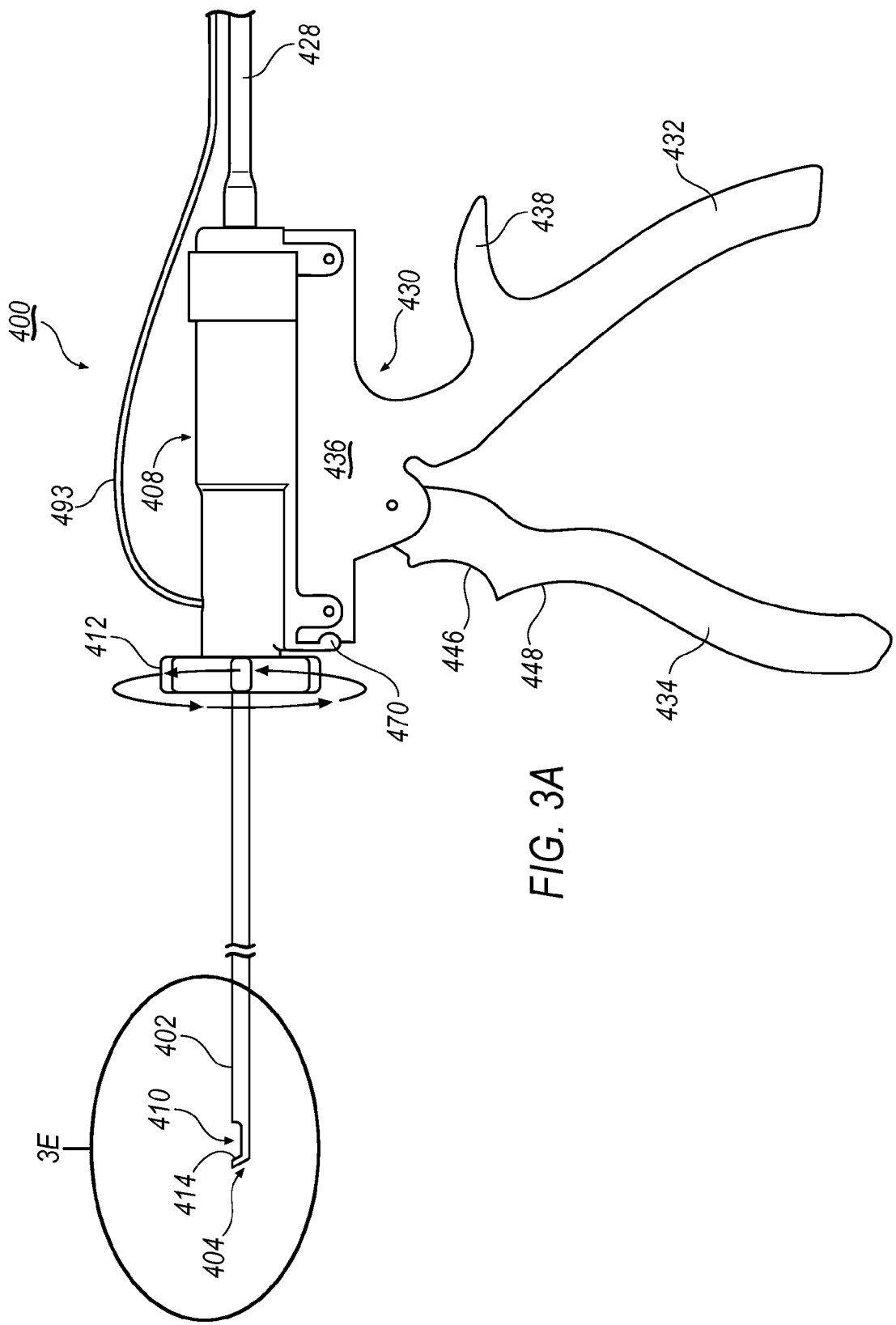
FIG. 3A is a side view of an alternative embodiment of an irrigating suction device.
Figure 3F:
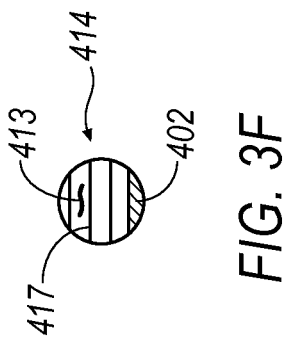
FIG. 3F is an end view of a foot plate taken along lines 3F-3F in FIG. 3E.
Figure 3G:
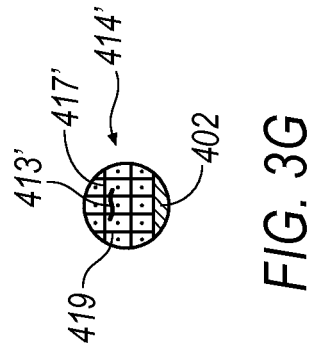
FIG. 3G is an alternative embodiment of the foot plate taken along lines 3F-3F in FIG. 3E.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is a method of tissue resection, as well as various components of a device used in same. The components disclosed herein provide surgeons with an enhanced ability to minimize trauma to the patient, while providing effective and efficient minimally invasive surgical techniques.

Referring to FIGS. 1A-1B, a first embodiment of a suction punch 200 is provided. A first embodiment of a suction punch 200 includes a base member 202 and a selectively slidable cutting member 204 that slides on base member 202. A distal end 206 of suction punch 200 extends upwardly from base member 202 and forms a cutting surface 208.

Suction punch 200 further comprises an actuator assembly 210. Actuator assembly 210 comprises a first gripping member 212 and a second gripping member 214. First gripping member 212 includes a first end 216 that is pivotally connected to a sleeve 218. A second end 220 of the first gripping member 212 may be configured as a gripping member with an opening 222 for receiving a finger or thumb. Second gripping member 214 includes a first end 224 that is fixedly connected to base member 202. A second end 226 of the second gripping member 214 may also be configured as a gripping member with an opening 228.

Slidable cutting member 204 is defined by an open distal end 230 and an open proximal end 232. Slidable cutting member 204 is moveable between an open position and a cutting position. In the open position, distal end 230 is spaced away from cutting surface 208 to create a tissue receiving opening 233, as seen in FIG. 1A. In the cutting position, distal end 230 is slid into contact with cutting surface 208, thereby effectively closing tissue receiving opening 233 and cutting tissue that prolapses within tissue receiving opening 233 (to be explained below).

Distal end 230 is configured with a cutting edge sufficiently sharp to sever tissue, as will be explained in further detail below. Proximal end 232 is configured to receive a fitting (not shown) that is attached to a tubing line (not shown) that is operatively connected to a vacuum source. Accordingly, vacuum is delivered through cutting member 204 (indicated by arrow V) during operation of suction punch 200. Sleeve 218 is fixedly connected to cutting member 204 adjacent proximal end 232.

In operation, distal end 206 of suction punch 200 is inserted into the patient positioned adjacent tissue of interest. To insure proper placement of suction punch 200, suction punch 200 may be placed in the closed position prior to insertion (so as not to drag or snag tissue on cutting surface 208). While being inserted, the vacuum source is on, but may be vented to atmosphere to also prevent tissue from being pulled into suction punch 200 until properly positioned. To permit venting, an aperture 233 (show in phantom) may be formed through a sidewall of cutting member 204. When suction punch 200 is in the open position, the aperture is unblocked, to permit venting of the device. When suction punch 200 is in the closed position, aperture 233 is sealed off, thereby retaining vacuum. In one exemplary embodiment, a sealing sleeve 235 may be provided, whereby the sealing sleeve 235 (shown in phantom) is fixedly connected to base 202 and cutting member 204 is configured to slide therethrough. As cutting member 204 moves distally, aperture 233 slides into sealing sleeve 235, which may include a pair of seals, such as O'rings, at either end thereof. Once received therein, aperture 235 is effectively sealed and vacuum is restored to suction drive 200. Other configurations to provide selective venting is also contemplated. Once positioned, the vacuum is restored (by closing off the vent) and the suction punch 200 is placed in the open position. The vacuum source mechanically draws tissue into the tissue receiving opening 233. Next, the first gripping member 212 is actuated towards the second gripping member 214, as indicated by arrow F. This action causes cutting member 204 to slide along the base member 202 such that distal end 230 of cutting member 204 moves toward cutting surface 208 as indicated by arrow C. In one exemplary embodiment, cutting surface 208 is provided with a cutting lip 236 that cooperates with the cutting edge formed on distal end 230 of cutting member 204 to cleanly sever tissue.

Because suction device 200 is configured to deliver vacuum to tissue receiving opening 233, each manual cutting action automatically delivers the severed portions of the tissue (such as turbinates 12 for an endonasal approach) away from the patient. In one embodiment, a tissue filter (not shown) may be provided for retaining the severed portions of tissue. The tissue filter may be directly attached to the proximal end 232 of suction device 200. Alternatively, the tissue filter may be positioned remotely and operatively connected to the suction device 200 by tubing.

Unlike prior art punch devices, such as the Kerrison punch, only a single insertion of suction device 200 is required to sever any tissue in the desired pathway. Indeed, multiple tissue cutting actions can be accomplished with a single insertion. Thus, suction device 200 permits a speedier procedure, as well as less trauma to the patient.

To prevent tissue from occluding suction device 200, base member 202 may further be provided with an irrigation channel 238. Irrigation channel 238 extends from an open proximal end 240 of base member 240. Proximal end 240 may be configured to receive a fitting that is connected to an irrigation supply by tubing (not shown). A suitable irrigation supply may include saline or ringers.

Irrigation channel 238 further comprises a distal end 242 that adjoins an elongated mating channel 244 (best seen in phantom in FIG. 1B) formed adjacent cutting surface 208 in distal end 206 of suction device 200. Mating channel 244 is in communication with an opening 246 that extends through cutting surface 208.

In operation, irrigation is provided through irrigation channel 238 and delivered to tissue receiving opening 233. As the tissue is being severed, irrigation is being delivered to the tissue removed from the patient's body, lubricating the tissue and serving as a flushing mechanism to deliver tissue through suction punch 200 and prevent occlusion. Further, as discussed above, vacuum may also be applied to flush the irrigation fluid out of patient as suction device 200 operates.

Components of an alternative arrangement of a base member 302 of a suction punch 300 is shown in FIGS. 3A-3B. FIG. 3A is a cross-sectional view of base member 302. As may be seen, base member 302 is connected to a distal end 306 of suction punch 300, which defines a cutting surface 308. A cutting lip 336 may also be provided on cutting surface 308.

Like suction punch 200, base member 302 of suction punch 300 includes an irrigation channel that extends from a proximal end 334 along the length of base member 302 to a distal end 342. At proximal end 334, irrigation channel 302 is operatively connected to an irrigation supply, as described above in connection with suction punch 200. At distal end 342, irrigation channel connects to a groove 344 that adjoins an opening 346 formed at a base 347 of cutting surface 308. Thus, in operation, irrigation fluid may be supplied to base 347 of cutting surface 308.

Yet another alternative embodiment of a suction punch 400 is shown in FIGS. 3A-5G. Suction punch 400 includes an outer cannula 402 defined by a distal end 404 and a proximal end 406 (seen best in FIG. 3C), which is seated within a housing member 408 (to be explained in further detail below). A tissue receiving opening 410 is formed in outer cannula 402 adjacent distal end 404. Outer cannula 402 is configured for selective rotational movement. More specifically, a rotation dial 412 is fixedly secured to an outer surface of outer cannula 402. In one particular embodiment, a glue interference is used to fix rotation dial 412 to outer cannula 402. As rotation dial 412 is rotated, tissue receiving opening 410 is also rotated, thereby allowing for easy manipulation of suction punch 400 during procedures. Formed at distal end 404 of outer cannula 402, distally of tissue receiving opening 410, is a cutting surface or foot plate 414.

Referring to FIG. 3C, disposed within outer cannula 402 is an inner cutting cannula 416. Inner cutting cannula 416 includes a cutting edge 418 disposed on a distal end 420 thereof. Cutting edge 418 cooperates with a distal edge 422 of tissue receiving opening 410 to sever tissue that is received within tissue receiving opening 410. A proximal end 424 of inner cutting cannula 416 is disposed in a fitting barb 426, to which a vacuum line 428 is operatively connected. Inner cutting cannula 416 is slidably seated within housing member 408. In other words, inner cutting cannula 416 is configured to selectively slide or reciprocate within outer cannula 402 during operation. However, inner cutting cannula 416 is also rotationally fixed with respect to outer cannula 402 such that rotation of rotation dial 412 also servers to rotate inner cutting cannula 416 with outer cannula 402.

Housing member 408 is mounted to an actuation member 430. Actuation member 430 comprises a first handle device 432 and a second handle device 434. First handle device 432 is fixedly connected to a shuttle housing 436. In one exemplary configuration, shuttle housing 436 is integrally formed with first handle device 432. First handle device 432 may further be configured with a thumb grip 438 for ease of use.

Second handle device 434 is pivotally connected to shuttle housing 436. Referring to FIG. 3B, a first end 440 is of second handle device 434 is received within a slot 442 that is formed within a selectively slidable shuttle member 444 that is disposed within shuttle housing 436. Second handle device 434 may be configured with gripping members 446 and 448 for ease of use.

Shuttle member 444 is mounted on a rod 450 (best seen in FIG. 3C) disposed in shuttle housing 436. Rod 450 is defined by a distal end 452 and a proximal end 454. Distal end 452 is fixedly secured to a distal face 456 of shuttle housing 436. Proximal end 454 is fixedly secured to a proximal face 458 of shuttle housing 436. A biasing member 460 is positioned on rod 450 distally of shuttle 444, so as to abut distal face 456 and a distal end of shuttle 444. Biasing member 460 (which may be a coil spring) serves to bias shuttle 444 into a retracted position, away from distal face 456. In one exemplary arrangement, a stop member 462 is secured to proximal end 454 of rod 450. Stop member 462 limits the distance that shuttle 444 may be retracted by biasing member 460. In one exemplary arrangement, actuation member 430 may be configured as a re-useable element.

Carried by, and fixedly secured to shuttle 444 is a carrier member 464. An end view of carrier member 464 is provided in FIG. 3D. Carrier member 464 includes upwardly extending wall members 466 that flank a mounting groove 468. Carrier member 464 extends upwardly from shuttle housing 436.

Housing member 408 is secured to shuttle housing 436. In one exemplary arrangement, housing member 408 includes a locking tab 470 that extends downwardly from housing member 408 and engages with a mounting groove 472 formed on a distal face 456 of shuttle housing 436. A proximal end 474 of housing member 408 may further include a downwardly extending wall member 476 that carries a snap protrusion 478 to grip a portion of the shuttle housing 436 (see FIG. 4B).

Disposed within housing member 408 is mounting sleeve 480. Mounting sleeve 480 comprises an elongated section 482 that is connected to a mounting section 484. Disposed on either side of mounting section 484 are flange members 486. Mounting section 484 is received within mounting groove 468 carrier member 464. A distal end 488 of elongated section 482 is slidably received within a channel 485 formed in a mating sleeve 487. Mounting sleeve 480 is fixed secured to an outside surface of inner cutting cannula 416. To insure that inner cutting cannula 416 rotates with outer cannula 402, elongated section 482 is provided with a keyed surface that mates with a corresponding keyed surface formed in channel 484 (not shown). Thus, inner cutting cannula 416 may still selectively slide within channel 484 (and ultimately outer cannula 402), but not rotate independently of mating sleeve 487.

An internal hub member 490 is provided within housing member 408. Hub member 490 has a first end fixed to rotary dial 412 and a second end fixed to mating sleeve 487. Proximal end 406 of outer cannula 402 is secured in hub member 490.

Formed through housing member 408 is an irrigation port 492 that is in communication with an opening 494 in the hub member 490. In operation, irrigation (such as warm water, saline or ringers) enters into housing member 408 and into hub member 490 to deliver irrigation within the space between the inner cutting cannula 416 and the outer cannula 402. Sealing members (not shown), such as O-rings, may be disposed in grooves 496 disposed on either side of opening 494 to insure that the irrigation is directed between outer cannula 402 and inner cutting cannula 416.

Disposed at the proximal end of suction punch 400 is a fitting member 498 that is disposed in a fitting housing 499. The fitting member 498 carries fitting barb 424 and is configured with mounting grooves 500 that receive seal members (not shown). As discussed above, a vacuum line 428 is connected to the fitting barb 424 to deliver vacuum to inner cutting cannula 416. The seal members that are disposed in grooves 500 serve to insure that the vacuum is delivered to the inner cutting cannula 416.

Inner cannula 416 may also be provided with a vent aperture 501 to provide selective venting of suction device 400. When inner cannula 416 is retracted from tissue receiving opening 410 (as shown in FIG. 3C), vent aperture 501 is opened. However, when inner cannula 416 is in a cutting position (i.e., when distal end 418 is contacting cutting surface 422), vent aperture 501 becomes sealed off. More specifically, in one exemplary mounting sleeve 480 i8s moved out of channel 485 of mating sleeve 487, at least enough to expose venting aperture 501 that extends through both mounting sleeve 480 and inner cannula 416. When inner cannula 416 is advanced during the cutting stroke, venting aperture 501 is received with mating sleeve 487, distally of a sealing member (not shown) disposed in mounting grooves 503. In this configuration full vacuum is delivered through inner cannula 416.

During operation of suction device 400, second handle device 434 is retracted towards first handle device 432. This action causes shuttle 444 to move forward, against biasing member 460. As shuttle 444 moves forward, carrier member 464 pushes against one of the flanges 486 of mounting sleeve 480. As mounting sleeve 480 is fixedly secured to an outer surface of inner cutting cannula 416, inner cutting cannula 416 is advanced distally within outer cannula 402 toward tissue receiving opening 410, until distal end 420 of inner cutting cannula 416 contacts foot plate 414 of outer cannula 402, thereby severing tissue that is disposed with tissue receiving opening 410. Repeated retraction and releasing of second handle device 434 results in repeated cutting action.

As discussed above, to facilitate severing of tissue, vacuum is delivered to inner cutting cannula 416 through vacuum line 428. The vacuum serves to draw tissue into tissue receiving opening 410, as well as removing cut tissue from tissue receiving opening 410 to a collection chamber (not shown)

attached to vacuum line 428. Continuous vacuum permits multiple severing actions to be employed with a single insertion. However, delivery of continuous vacuum may be controlled by the action of the cutting cannula. More specifically, the action of the inner cutting cannula provides for a venting action that relieves vacuum. As such, the device is particularly useful in navigating near and around critical structures within the patient so as not to inadvertently remove such structures during procedures. In addition, by providing the capability of multiple severing actions, procedure time may be reduced.

To alleviate removed tissue occluding the aspiration pathway during the cutting action, irrigation may be provided via an irrigation port 492 that is connected to an irrigation supply by an irrigation line 493, between the inner cutting cannula 416 and the outer cannula 402. The irrigation fluid, which may be warm water, saline, lactated ringers, or solutions intended to further enhance the biological preservation or integrity of the severed tissue may be used to flush the tissue during the procedure. To provide flexibility in accessing the soft tissue or boney tissue structure, rotation dial 412 permits the user to selectively rotate tissue receiving opening 410 to a desired location within the nasal cavity 14.

To prevent tissue that is to be cut from slipping away from foot plate 414 when cutting cannula 416 is advanced toward foot plate 414 during the cutting stroke, a contact face 413 of foot plate 414 is provided with a textured surface that is designed to grip tissue. In one exemplary arrangement, the textured surface of foot plate 414 includes at least one serration 415 formed on contact face 413. In one exemplary arrangement the serration 415 may be configured as a raised ramp with a proximally outwardly extending peak 417. Peak 417 may be configured to extend substantially across the entire width of contact face 413. However, it is understood that peak 417 need not extend across the entire width of contact face 413. In yet another alternative and exemplary configuration, referring to FIGS. 5A-5B, inverted serrations also be formed on foot plate 414. Inverted serrations will be discussed in further detail below.

Figure 3E:
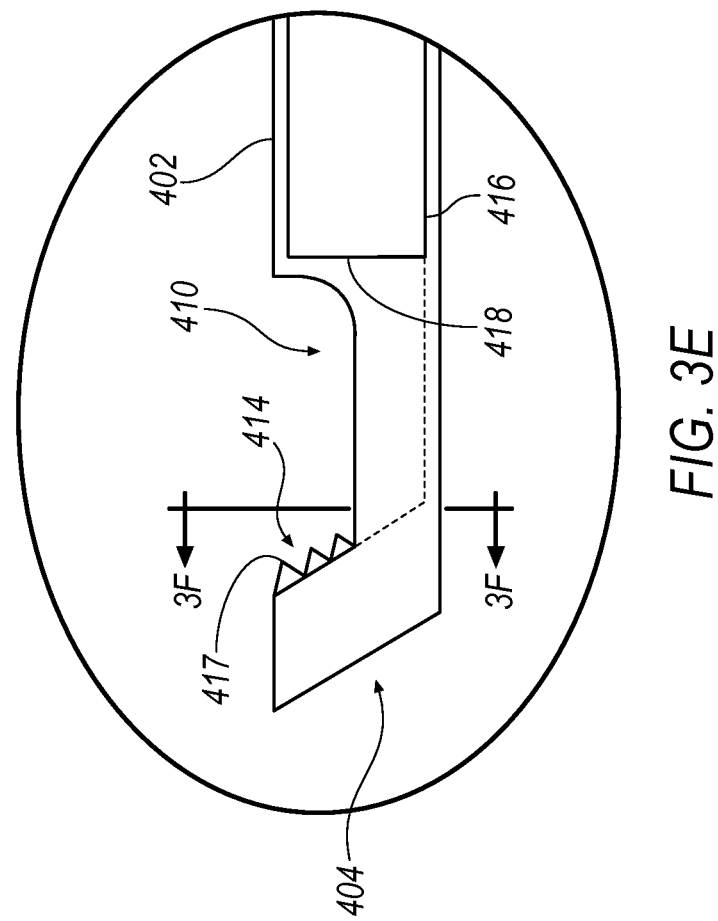
FIG. 3E is an enlarged view of area 3E taken from FIG. 3A.

In yet another embodiment, a plurality of serrations 415 formed on contact face 413 that are configured as a series of raised ramps terminating at outwardly facing peaks 417, such as, for example shown in FIG. 3E. As discussed above, each peak 417 may be configured to extend substantially across the entire contact face 413. Alternatively, peak 417 may be configured with interruptions such that a plurality of separate outwardly extending peaks 417 may be formed along a plane.

In another exemplary configuration, the textured surface of foot plate 414' includes a waffle pattern that has first and second intersecting contact edges 417' and 419, respectively. In one exemplary arrangement, the waffle pattern is positioned on contact face 413' such that first contact edge 417' is oriented so as to be generally horizontal and second contact edge 419 is oriented so as to be generally vertical. However, it is understood that the disclosure is not limited to this particular configuration. Indeed, other orientations are also possible. It is further understood that the present disclosure is also not limited to the particular textured surface configurations described herein (i.e., the serrations 415 and the waffle pattern comprising first and second contact edges 417' and 419). Any textured surface that may operate as a gripping surface is within the scope of this disclosure.

The texture surface for foot plate 414 may be manufactured in a number of different manners. For example, textured contact surface 413/413' may be manufactured using a material removal process such as, for example, milling, grinding, knurling, bead blasting, sand blasting or pitting. Alternatively, texture contact surface 413/413' may be manufactured using an additive fabrication process such as, for example, beading. Further, textured contact surface 413/413' may be formed during a casting operation, such as sintering, stamping, investment casting, press molding, or die casting.

The textured contact surface 413/413' permits use of the an angled foot plate 414 (as may be seen in FIG. 3E), thereby permitting foot plate 414 to be effectively used in a shoveling manner to easily and quickly get underneath tissue and/or boney material to be cut. More specifically, because contact surface 413/413' is textured, contact surface 413/413' serves as a grip to frictionally retain tissue and/or boney material against contact surface 413/413' as cutting cannula 416 is advanced toward foot plate 414 during a cutting stroke. In one exemplary configuration, foot plate 414 is angled approximately 40°, although it is understood that other angled configurations are also possible.

Yet another alternative embodiment of a suction punch 400 is shown in FIGS. 4A-4K. Suction punch 1400 includes an outer cannula 1402 defined by a distal end 1404 and a proximal end 1406 (best seen in FIG. 4F), which is seated within a housing member 1408 (to be explained in further detail below). Distal end 1404 is open and may have an angled cutting edge 1414 to provide increased cutting effectiveness, to be explained below in further detail.

Outer cannula 1402 is configured for selective rotational movement. More specifically, a rotation dial 1412 is operatively secured to outer cannula 1402 (to be explained below in further detail). As rotation dial 1412 is rotated, distal end 1404 is also rotated, thereby allowing for easy manipulation of suction punch 1400 during procedures. Outer cannula 1402 is also configured for reciprocal movement, also to be explained below in further detail.

Figure 4D:
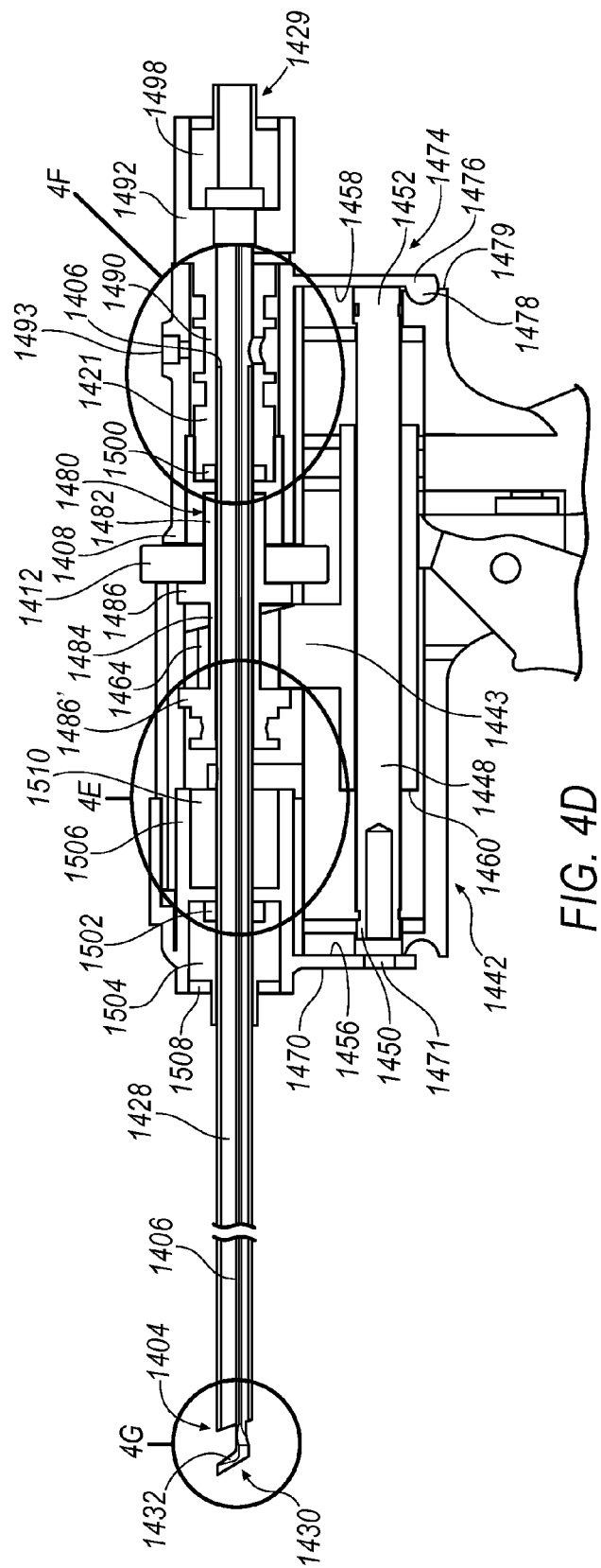
FIG. 4D is a cross-sectional view of the irrigating suction device of FIG. 4A.

Referring to FIG. 4D, disposed within outer cannula 1402 is an inner blade 1416. Inner blade 1416 is axially fixed with respect to housing 1408, such that it does not reciprocate. In one exemplary embodiment, (shown in FIGS. 4D and 4F), a proximal end 1418 of inner blade 1416 includes an attachment lip 1419 that is fixed to a portion of a saline hub 1421 (to be described in further detail below) positioned in housing 1408. In another exemplary embodiment, proximal end 1418 may be formed with an attachment hole (not shown) that aligns with attachment passage 1420, wherein both the attachment hole and the attachment passage receive an attachment mechanism, such as a pin.

Figure 4F:
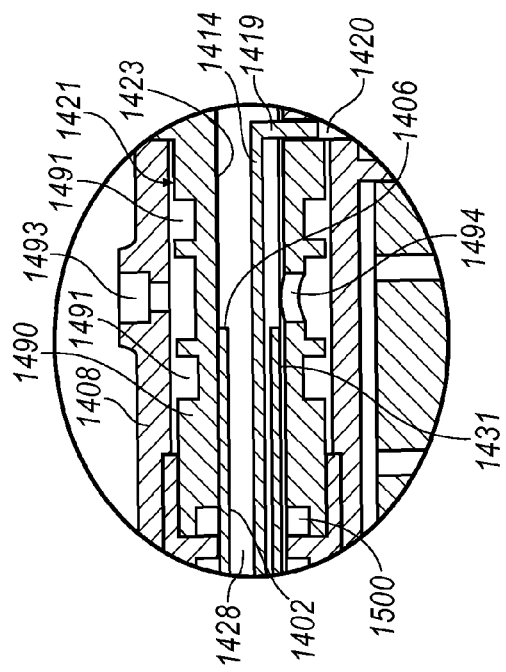
FIG. 4F is an enlarged cross-sectional view of area 4F from FIG. 4D.
Figure 4H:
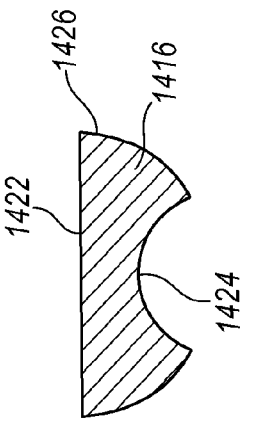
FIG. 4H is a cross-sectional view of an inner blade taken along lines 4H-4H in FIG. 4G.
Figure 4E:
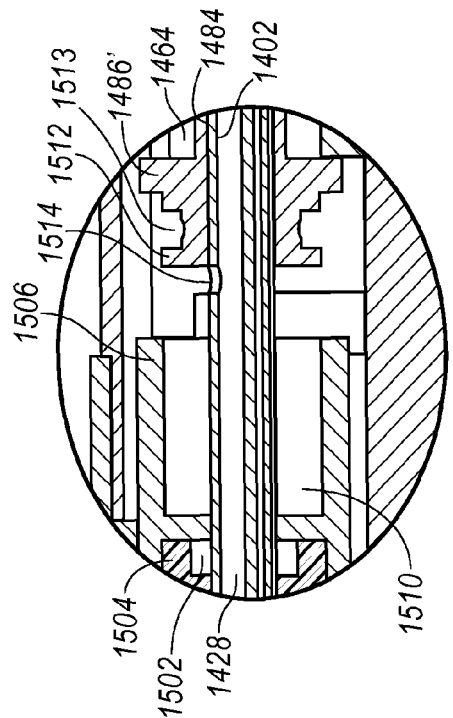
FIG. 4E is an enlarged cross-sectional view of area 4E from FIG. 4D.
Figure 4G:
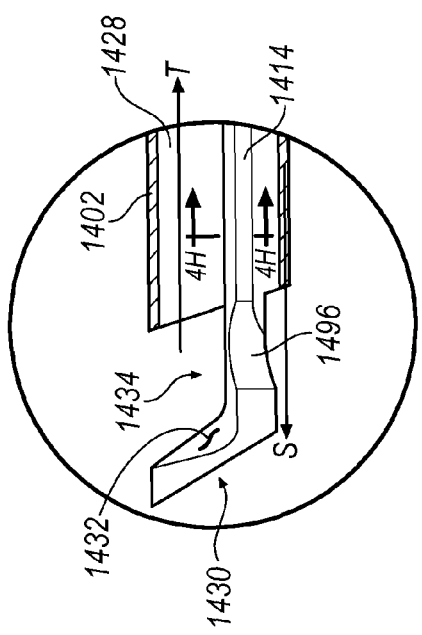
FIG. 4G is an enlarged cross-sectional view of area 4G from FIG. 4D.

FIG. 4H illustrates a cross-section of inner blade 1416 taken along lines 4H-4H in FIG. 4G. Inner blade 1416 is defined by a top surface 1422, a grooved surface 1424, and a curved bearing surface 1426. Top surface 1422 cooperates with an inner lumen 1428 of outer cannula 1402 to form a tissue passage (to be explained in further detail below). Grooved surface 1424 cooperates with inner lumen 1428 of outer cannula 1402 to form a saline passage. Positioned adjacent a distal end 1430 is a saline opening 1496 that is in communication with the saline passage. Curved bearing surface 1426 generally corresponds to the contour of inner lumen 1428. A portion 1431 of curved bearing surface 1426 serves as a glue surface to fixedly attach inner blade 1416 to saline hub 1421. Indeed, inner blade 1416 is fixedly secured to an inner surface of saline hub 1421, which is mounted in housing 1408, such that inner blade 1416 is axially fixed with respect to housing 1408.

A distal end 1430 of inner blade 1416 includes a cutting surface or foot plate 1432 that extends upwardly from top surface 1422. Cutting surface/foot plate 1432 cooperates with cutting edge 1414 of outer cannula 1402 to sever tissue that is received within a gap 1434 formed between distal end 1430 of inner blade 1416 and distal end 1404 of outer cannula 1402.

Referring to FIG. 4A, housing member 1408 is mounted to an actuation member 1436. Actuation member 1436 comprises a first handle device 1438 and a second handle device 1440. First handle device 1438 is fixedly connected to a shuttle housing 1442. In one exemplary configuration, shuttle housing 1442 is integrally formed with first handle device 1438. First handle device 1438 may be configured with a thumb grip (not shown), similar to that shown in FIG. 3A (438).

Second handle device 1440 is pivotally connected to a shuttle member 1443 disposed within shuttle housing 1442. Second handle device 1440 may be configured with gripping members 1444, 1446.

Referring to FIG. 4D, shuttle member 1443 is mounted on a rod 1448 disposed in shuttle housing 1442. Rod 1448 is defined by a distal end 1450 and a proximal end 1452. Distal end 1450 is fixedly secured to an interior distal face 1456 of shuttle housing 1442. Proximal end 1452 is fixedly secured to an interior proximal face 1458 of shuttle housing 1442. A biasing member (not shown) is positioned on rod 1448 distally of shuttle member 1443, so as to abut distal face 1456 and a distal end 1460 of shuttle member 1443. Biasing member (which may be a coil spring) serves to bias shuttle member 1443 into a retracted position, away from distal face 1456. A stop member (not shown) may be secured to proximal end 1452 of rod 1448 to limit the distance that shuttle member 1443 may be retracted by the biasing member.

Carried by, and fixedly secured to shuttle member 1443 is a carrier member 1464. Carrier member 1464 is similar to carrier member 464 shown in FIG. 3D, and includes upwardly extending wall members that flank a mounting groove. Carrier member 1464 extends upwardly from shuttle housing 1442.

Housing member 1408 is secured to shuttle member 1443. As best seen in FIG. 4D, in one exemplary arrangement, housing member 1408 includes a mounting flange 1470 that extends downwardly from housing member 1408. A fastening device (not shown) is engaged through a mounting channel 1471 that extends through mounting flange 1470. The fastening device further extends through rod 1448 to secure rod 1448 to housing member 1408.

A proximal end 1474 of housing member 1408 further includes a downwardly extending wall member 1476 that may carry a locking tab 1478. Locking tab 1478 engages with a mounting groove 1479 formed on a proximal face of shuttle member 1443.

Disposed within housing member 1408 is mounting sleeve 1480. Mounting sleeve 1480 comprises an elongated section 1482 that is connected to a mounting section 1484. Disposed on either side of mounting section 1484 are flange members 1486 and 1486'. Mounting section 1484 is received within a mounting groove formed on carrier member 1464. Extending through mounting flanges 1486, 1486' and mounting sleeve 1480 is a passage that receives outer cannula 1402. Outer cannula 1402 is fixedly secured within the passage. In one exemplary arrangement, outer cannula 1402 may be fixedly secured within the passage by glue. Fixedly secured to an outer surface of elongated section 1482 of mounting sleeve 1480 is rotation dial 1412. With this arrangement, as rotation dial 1412 is rotated, mounting sleeve 1480 will rotate, as well. Further, because outer cannula 1402 is fixed secured to mounting sleeve 1480, as rotation dial 1412 is rotated, outer cannula 1402 will also rotate.

Referring now to FIG. 4F, saline hub 1421 will now be described. Saline hub 1421 includes an internal hub portion 1490 and an external hub portion 1492 (best seen in FIG. 4D). Saline hub 1421 is mounted to proximal end 1474 of housing 1402 such that internal hub portion 1490 is disposed within housing 1408. A channel 1423 extends through saline hub 1421 and is in communication with an irrigation opening 1494 formed through saline hub 1421. Channel 1423 is configured to receive outer cannula 1402. Outer cannula 1402 is mounted within channel 1423 for sliding engagement. Inner blade 1416 is also received within channel 1423, as described above. Inner lumen 1428 of outer cannula 1402 opens into channel 1423 at distal end 1406 of outer cannula 1402.

Formed through housing member 1408 is an irrigation port 1493. Irrigation port 1493 is operatively connected to an irrigation line 1495 and is in communication with irrigation opening 1494 in saline hub 1421. In operation, irrigation (such as warm water or saline) enters into housing member 1408 and into saline hub 1421 to deliver irrigation within the space between inner blade 1416 and outer cannula 1402, along a channel formed by grooved surface 1424 and inner lumen 1428. Irrigation flows up through a saline opening 1496 formed in distal end 1430 of inner blade 1416 to deliver irrigation within gap 1434 between inner blade 1416 and outer cannula 1402. Sealing members (not shown), such as O-rings, may be disposed in grooves 1491 disposed on either side of irrigation opening 1494 to insure that the irrigation is directed to the channel formed by grooved surface 1424 and inner lumen 1428 of outer cannula 1402.

Disposed at proximal end 1474 of suction punch 1400 is a fitting member 1498 that is disposed in external hub portion 1492. Fitting member 1498 carries a fitting barb 1499. A vacuum line (not shown) is connected to the fitting barb 1499 to deliver vacuum to outer cannula 1402. To insure that vacuum is delivered to outer cannula 1402, and ultimately to a distal end 1404 of outer cannula 1402, suction punch 1400 is provided with seal members disposed within housing 1408. More specifically, in one exemplary arrangement, saline hub 1421 is provided with grooves 1500 disposed at a distal end thereof that receives seal members (not shown). And additional set of grooves 1502 is provided in a distal housing hub 1504 (shown in FIG. 4D). Distal housing hub 1504 is mounted in a first mounting portion 1506 of housing 1408. First mounting portion 1506 further includes a distal chamber 1508 and a proximal chamber 1510. Distal housing hub 1504 is mounted in distal chamber 1508. Proximal chamber 1510 is configured to receive a distal sealing end 1512 of mounting sleeve 1480. A mounting groove 1513 is formed between distal sealing end 1512 and flange member 1486'. Mounting groove 1513 receives a sealing member (not shown) such as an O-ring. In one embodiment, positioned adjacent to mounting sleeve 1480 is a venting aperture 1514 (best seen in FIG. 4E). Venting aperture 1514 extends through a sidewall of outer cannula 1402.

During operation of suction device 1400, second handle device 1440 is retracted towards first handle device 1438. This action causes shuttle member 1443 to move forward, against the biasing member. As shuttle member 1443 moves forward, carrier member 1464 pushes against one of the flanges 1486' of mounting sleeve 1480. Because mounting sleeve 1480 is fixedly secured to an outer surface of outer cannula 1402, outer cannula 1402 is advanced distally over inner blade 1416, until distal end 1404 of outer cannula 1402 contacts cutting surface 1432 of inner blade 1416, thereby severing tissue that is disposed with gap 1434 defined between inner blade 1414 and distal end 1404 of outer cannula 1402 (see FIG. 4B). Repeated retraction and releasing of second handle device 1440 results in repeated cutting action.

To facilitate collection of tissue, vacuum is delivered to outer cannula 1402 through a vacuum line attached to fitting barb 1499. The vacuum serves to draw tissue into outer cannula 1402, as well as remove cut tissue to a collection chamber (not shown) attached to the vacuum line. Continuous vacuum permits multiple severing actions to be employed with a single insertion. However, delivery of continuous vacuum may be controlled by the action of the cutting cannula. More specifically, the action of the inner cutting cannula provides for a venting operation that relieves vacuum. As such, the device is particularly useful in navigating near and around critical structures within the patient so as not to inadvertently remove such structures during procedures. In addition, by providing the capability of multiple severing actions, procedure time may be reduced.

To alleviate removed tissue occluding the aspiration pathway during the cutting action, irrigation may be provided via an irrigation port 1493 that is connected to an irrigation supply by irrigation line 1495, between inner blade 1416 and outer cannula 1402. The irrigation fluid, which may be warm water or saline, can flow up through opening 1496 in inner blade 1416. Such fluid serves to flush the tissue during the procedure. To provide flexibility, such as to access turbinates 12 in an endonasal procedure, rotation dial 1412 permits the user to selectively rotate inner blade 1416 and outer cannula 1402 to a desired location within a body cavity.

Suction punch 1400 may also provide vacuum relief during operation. During the cutting stroke, as second handle device 1440 is actuated and distal end 1404 of outer cannula 1402 is moved toward cutting surface 1432 of inner blade 1416, distal sealing end 1512 of mounting sleeve 1480 moves into proximal chamber 1510 of first mounting portion 1506 until flange member 1486' abuts first mounting portion 1506, with a sealing member (disposed within mounting groove 1513) contacting an inner surface of proximal chamber 1510. Venting aperture 1514, which is positioned distally of distal sealing end 1512, is thus sealed off while outer cannula 1402 is engaged with cutting surface 1432 of inner blade, providing full vacuum to deliver severed tissue through outer cannula 1402.

To provide vacuum relief, as second handle device 1440 is returned to its non-actuated position (i.e., away from first handle device 1438) by the biasing member, distal sealing end 1512 of mounting sleeve 1480 is moved out of proximal chamber 1510, thereby allowing vacuum delivered through outer cannula 1402 to vent through vent aperture 1514.

Turning to FIGS. 4I-4K, partial illustrations of an alternative configuration of a suction punch 1600 are shown. Suction punch 1600 is very similar to suction punch 1400 and includes an outer cannula 1602 that is configured similar to outer cannula 1402. Outer cannula 1602 is defined by a distal end 1604 and a proximal end 1606 (see in FIG. 4K), which is seated within a housing member similar to housing member 1408. Distal end 1604 is open and may have an angled cutting edge 1614 to provide increased cutting effectiveness. Outer cannula 1602 is configured for both selective rotational movement and reciprocal movement by an actuation assembly, as described above in connection with suction punch 1400.

Disposed within outer cannula 1602 is an inner cannula 1616. In the configuration shown in FIG. 4I, inner cannula 1616 replaces inner blade 1416. Inner cannula 1616 is axially fixed with respect to the housing, such that it does not reciprocate. In one exemplary arrangement, a portion of a proximal end 1619 of inner cannula 1616 includes an outwardly extending mounting member that may be received within a portion of a saline hub 1621 positioned in housing 1608 (see, e.g., FIG. 4K). In one configuration, the mounting member is received within a mounting groove 1620. The mounting member may be secured within mounting groove 1620 with glue to fixedly attach inner cannula 1616 to housing 1408. A portion of an outer surface of inner cannula 1616 may serve as a glue surface to fixedly attach inner cannula 1616 to a portion of an inner surface 1622 of saline hub 1621, which is mounted in housing 1408, such that inner cannula 1616 is axially fixed with respect to housing 1408.

Inner cannula 1616 further is defined by a distal end 1630, which includes a cutting surface/foot plate 1632 disposed on a tip 1633 thereof. A tissue receiving opening 1635 is formed adjacent tip 1633. Cutting surface/foot plate 1632 cooperates with cutting edge 1614 of outer cannula 1602 to sever tissue that is received within tissue receiving opening 1635. Tissue receiving opening 1635 opens into a tissue passage 1637. Tissue passage 1637 is operatively connected to a vacuum supply. Vacuum supply operates to deliver severed tissue through the housing and to a collection canister.

Fixedly disposed within inner cannula 1616 is an irrigation supply tube 1639. In one exemplary configuration, irrigation supply tube 1639 is positioned along a bottom portion of inner cannula 1616 and has a distal end 1640 that is positioned adjacent cutting surface 1632. A proximal end 1634 of irrigation supply tube 1639 is in fluid communication with an irrigation opening 1694 disposed within saline hub 1621. More specifically, irrigation supply tube 1639 includes an opening 1636 formed in a sidewall that aligns with a corresponding opening 1638 formed inner cannula 1616. While irrigation supply tube 1639 is shown as being positioned along a bottom portion of inner cannula 1616, it is understand that the disclosure is not limited to that configuration. For example, and without limitation, irrigation supply tube 1639 may also be positioned along a top portion of inner cannula 1616 such that distal end 1640 is positioned at tissue opening 1635.

Referring now to FIG. 4K, saline hub 1621 will now be described. Saline hub 1621 includes an internal hub portion 1690. Saline hub 1621 is mounted to a proximal end of housing 1402 such that internal hub portion 1690 is disposed within housing 1408. A channel, defined by inner surface 1622 of saline hub 1621 extends through saline hub 1621. The channel is configured to receive outer cannula 1602. Outer cannula 1602 is mounted within the channel for sliding engagement. Inner cannula 1614 is also received within the channel, as described above.

Formed through housing member 1608 is an irrigation port 1693. Irrigation port 1693 is operatively connected to an irrigation line and is in communication with irrigation opening 1694 in saline hub 1621. In operation, irrigation (such as warm water or saline) enters into housing member 1608 and into saline hub 1621 to deliver irrigation to irrigation supply tube 1639. To direct irrigation fluid into irrigation supply tube 1639, sealing members (not shown), such as O-rings, may be disposed in grooves 1691, 1695 disposed on either side of irrigation opening 1694. More specifically, grooves 1691 are disposed in an outer surface of saline hub 1621 such that a sealing member disposed therein serves to prevent irrigation fluid from entering between saline hub 1621 and housing 1608. Grooves 1695 are disposed in inner surface 1622 of saline hub 1621 such that a sealing member disposed therein serves to prevent irrigation fluid from entering between inner and outer cannulas 1616, 1602.

Figure 4M:
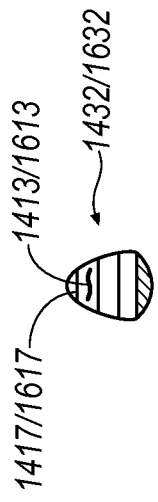
FIG. 4M is an end view of a foot plate taken along lines 4M-4M in FIG. 4L.
Figure 4N:
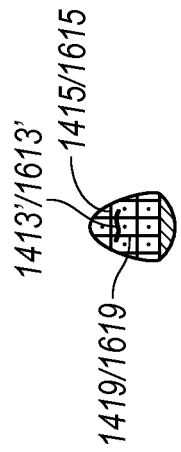
FIG. 4N is an alternative embodiment of the foot plate taken along lines 4N-4N in FIG. 4L.
Figure 4L:
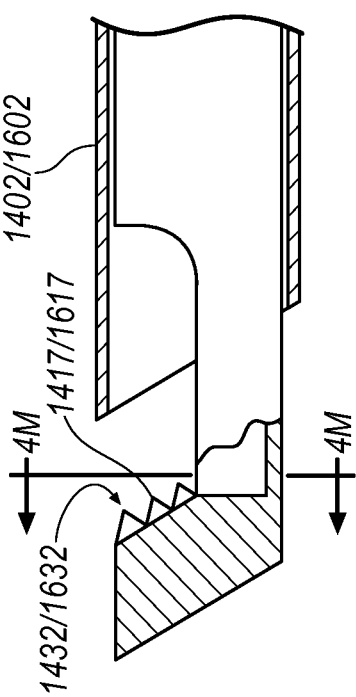
FIG. 4L is a partial cross-sectional view of an alternative configuration for a distal end of the irrigation suction punch such as that illustrated in either FIGS. 4A-4H or FIGS. 4I-4K.
Figure 5B:
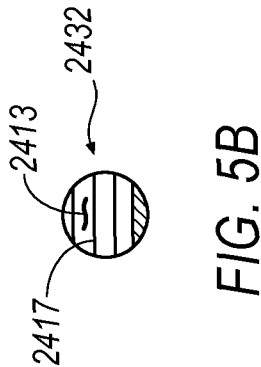
FIG. 5B is an end view of the foot plate taken along lines 5B-5B in FIG. 5A.

Turning now to FIGS. 4L-4N, to prevent tissue that is to be cut from slipping away from foot plates 1432/1632 when cutting cannula 1402/1602 is advanced toward foot plate 1432/1632 during a cutting stroke, a contact face 1413/1613 of foot plate 1402/1602 is provided with a textured surface that is designed to grip tissue, similar as to that which was described above in connection with FIGS. 3E-3G. More specifically, in one exemplary arrangement, the textured surface of foot plate 1432/1632 includes a plurality of serrations formed on contact face 1413/1613 that are configured as a series of ramp-like members terminating at outwardly facing peaks 1417/1617, such as, for example shown in FIG. 4L. In another exemplary configuration, the textured surface of foot plate 1432/1632 includes a waffle pattern that has first and second intersecting contact edges 1415/1615 and 1419/1619, respectively. In one exemplary arrangement, the waffle pattern is positioned on contact face 1413'/1613' such that first contact edge 1415/1615 is oriented so as to be generally horizontal and second contact edge 1419/1619 is oriented so as to be generally vertical. However, it is understood that the disclosure is not limited to this particular configuration. Indeed, other orientations are also possible.

Figure 6B:
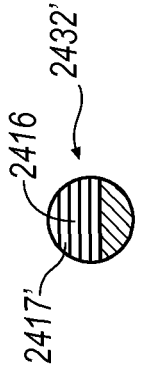
FIG. 6B is an end view of the foot plate taken along lines 6B-6B in FIG. 6A.
Figure 5A:
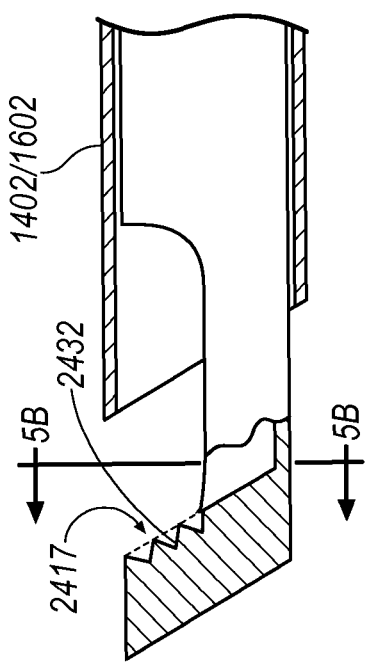
FIG. 5A is partial cross-sectional view of an alternative configuration for a distal end of the irrigation suction punch such as that illustrated in either FIGS. 4A-4H or FIGS. 4I-4K.
Figure 6A:
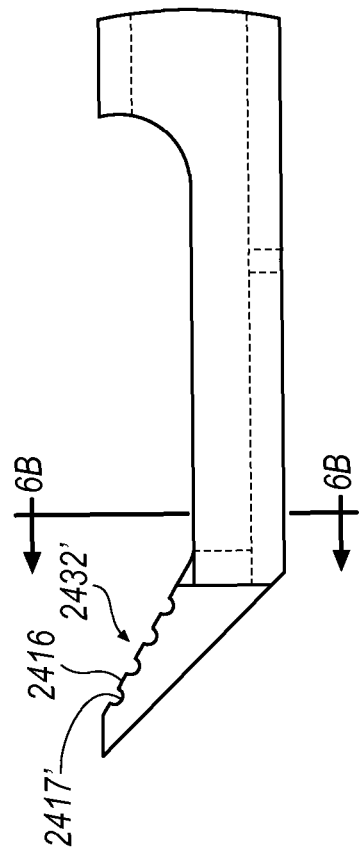
FIG. 6A is a partial cross-sectional view of an alternative configuration for a distal end of the irrigation suction punch, as that illustrated in either FIGS. 4A-4H or FIGS. 4I-4K.

It is further understood that the present disclosure is also not limited to the particular textured surface configurations described herein (i.e., the serrations comprising ramp-like members terminating at outwardly facing peaks 1417/1617 and the waffle pattern comprising first and second contact edges 1415/1615 and 1419/1619). Indeed, any textured surface that may operate as a gripping surface is within the scope of this disclosure. For example, referring to FIGS. 5A-5B, a contact face 2413 of foot plate 2432 may be provided with a plurality of inverted serrations formed on contact face 2413. Inverted serrations that are also configured as a series of ramp-like members, but ramp-like members terminate at inwardly facing valleys 2417, such as, for example shown in FIG. 5A. In yet another alternative arrangement, referring to FIGS. 6A-6B, contact face 2432' of foot plate 2432' may be provided with a plurality of inwardly extending grooves 2417' that are separated from one another by land members 2416, such as, for example shown in FIGS. 6A-6B.

In yet another alternative arrangement, shown in FIGS. 7A-7B, textured surface of contact face 3413 of foot plate 3432 may be formed by the use of a coarse grit coating, such as by sand blasting. While FIGS. 7A-7B illustrate only the coarse grit coating being used on contact face 3413, it is understood that in another exemplary arrangement, the coarse grit coating may be used with any other embodiments shown in FIGS. 4L-4N, 5A-5B and 6A-6B.

The textured surface for foot plate 1432/1632/2432/2432' may be manufactured in a number of different manners. For example, textured contact faces 1413/1613/2413 and 1413'/1613'/2413' may be manufactured using a material removal process such as, for example, milling, grinding, knurling, bead blasting, sand blasting or pitting. Alternatively, texture contact surfaces 1413/1613/2413 and 1413'/1613'/2413' may be manufactured using an additive fabrication process such as, for example, beading. Further, textured contact surfaces 1413/1613/2413 and 1413'/1613'/2413' may be formed during a casting operation, such as sintering, stamping, investment casting, press molding, or die casting.

The textured contact surfaces 1413/1613 and 1413'/1613' permit use of the an angled foot plate 1432/1632 (as may be seen in FIGS. 4B and 4I), thereby permitting foot plate 1432/1632 to be effectively used in a shoveling manner to easily and quickly get underneath tissue and/or boney material to be cut. More specifically, because contact surfaces 1413/1613 and 1413'/1613' are textured, contact surfaces 1413/1613 and 1413'/1613' serve as a grip to frictionally retain tissue and/or boney material against contact surfaces 1413/1613 and 1413'/1613' as outer cannulas 1402/1602 are advanced toward foot plate 1432/1632 during a cutting stroke. In one exemplary configuration, foot plates 1432/1632 are angled approximately 40°, although it is understood that other angled configurations are also possible.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A tissue cutting device, comprising:
   a housing;
   a cutting member partially supported within the housing, the cutting member defined by an open distal end and an open proximal end, the cutting member operatively connected to an actuator assembly;
   a hollow non-reciprocating base member partially supported within the housing, the hollow non-reciprocating base member defined by an open proximal end and having a hollow tissue pathway defined between a distal end of the hollow non-reciprocating base member and the open proximal end, having an upwardly extending foot plate disposed on the distal end thereof, the base member configured for selective rotation with respect to the housing;
   wherein the cutting member is configured for reciprocating movement with respect to the distal end of the hollow non-reciprocating base member;
   wherein the cutting member is received over the hollow non-reciprocating base member and is configured for selective rotational movement with respect to the housing;
   wherein a distal end of the cutting member has a cutting element and the distal end of the cutting member and the foot plate cooperates to define a tissue receiving opening;

wherein the foot plate defines a contact surface that is configured with a textured surface that serves as a grip to operatively retain material to be cut when the cutting member is moved toward the foot plate; and wherein when the cutting element of the cutting member is moved against the foot plate to sever tissue, the tissue that is severed is delivered through the hollow tissue pathway and out the proximal end of the hollow non-reciprocating base member to exit the housing by application of vacuum to the proximal end of the hollow non-reciprocating base member.

2. The tissue cutting device of claim 1, wherein the foot plate is oriented such that the foot plate is angled with respect to a horizontal axis extending through the hollow non-reciprocating base member in a distal direction by a predetermined amount.

3. The tissue cutting device of claim 2, wherein the foot plate is angled by approximately 40 degrees from a horizontal axis extending through the hollow non-reciprocating base member.

4. The tissue cutting device of claim 1, wherein the textured surface is configured as at least one serration that defines at least one extending peak.

5. The tissue cutting device of claim 4, wherein the at least one peak is configured to extend proximally from the contact surface.

6. The tissue cutting device of claim 4, wherein the at least one serration is inverted such that the at least one peak extends inwardly from the contact surface.

7. The tissue cutting device of claim 4, wherein the textured surface is configured with a plurality of serrations, each serration defined by a peak.

8. The tissue cutting device of claim 4, wherein the peak is oriented so as to be generally horizontal with respect to the contact surface.

9. The tissue cutting device of claim 7, wherein each peak extends across the width of the foot plate.

10. The tissue cutting device of claim 7, wherein each peak is discontinuous across the width of the foot plate.

11. The tissue cutting device of claim 1, wherein the textured surface is configured to include at least one groove formed in the contact surface.

12. The tissue cutting device of claim 11, wherein the textured surface is configured with a plurality of grooves formed in the contact surface, wherein each groove is separated by a land member.

13. The tissue cutting device of claim 1, wherein the textured surface is formed using a material removal operation.

14. The tissue cutting device of claim 13, wherein the material removal operation is one of milling, grinding, knurling, bead blasting, sand blasting and pitting.

15. The tissue cutting device of claim 1, wherein the textured surface is formed using a casting operation.

16. The tissue cutting device of claim 15, wherein the casting operation is one of sintering, stamping, investment casting, press molding, and die casting.

17. The tissue cutting device of claim 1, wherein the textured surface is formed by a beading operation.

18. The tissue cutting device of claim 1, wherein the textured surface is configured as waffle pattern that is defined by a plurality of first and second proximally extending intersecting contact edges.

19. The tissue cutting device of claim 18, wherein the first contact edges are oriented to extend generally horizontally and the second contact edges are oriented to extend generally vertically.

20. The tissue cutting device of claim 18, wherein the waffle pattern is formed using a material removal operation.

21. The tissue cutting device of claim 20, wherein the material removal operation is one of milling, grinding, knurling, bead blasting, sand blasting and pitting.

22. The tissue cutting device of claim 18, wherein the waffle pattern is formed using a casting operation.

23. The tissue cutting device of claim 22, wherein the casting operation is one of sintering, stamping, investment casting, press molding, and die casting.

24. The tissue cutting device of claim 18, wherein the waffle pattern is formed by a beading operation.

25. The tissue cutting device of claim 1, wherein the textured surface is configured as a coarse grit coating that is applied to the contact face.

26. The tissue cutting device of claim 4, further including a coarse grit coating applied to the contact face, including the at least one serration.

27. The tissue cutting device of claim 11, further including a coarse grit coating applied to the contact surface, including the at least one groove.

28. The tissue cutting device of claim 18, further including a coarse grit coating applied to the contact surface, including the first and second proximally extending intersecting contact edges.

29. The tissue cutting device of claim 1, further comprising an irrigation supply tube positioned along a portion of the hollow non-reciprocating base member, wherein the irrigation supply tube includes a distal end that is positioned adjacent the contact surface.

* * * * *

UNITED STATES PATENT AND TRADEMARK OFFICE
CERTIFICATE OF CORRECTION

| | |
|---|---|
| PATENT NO. | : 8,986,334 B2 |
| APPLICATION NO. | : 12/966327 |
| DATED | : March 24, 2015 |
| INVENTOR(S) | : Joseph L. Mark et al. |

Page 1 of 1

It is certified that error appears in the above-identified patent and that said Letters Patent is hereby corrected as shown below:

In the Claims

Column 16, Claim 25, line 32, please change [[face]] to --surface--.
Column 16, Claim 26, line 34, please change [[face]] to --surface--.

Signed and Sealed this
Thirtieth Day of June, 2015

Michelle K. Lee
*Director of the United States Patent and Trademark Office*